United States Patent [19]
Ohnishi et al.

[11] Patent Number: 5,502,293
[45] Date of Patent: Mar. 26, 1996

[54] HEATER ELEMENT FOR A TUBE CONNECTING DEVICE

[75] Inventors: Shuichi Ohnishi, Fuji; Atsushi Suzuki, Yamanashi, both of Japan

[73] Assignee: Terumo Kabushiki Kaisha, Tokyo, Japan

[21] Appl. No.: 66,430

[22] Filed: May 25, 1993

[30] Foreign Application Priority Data

May 26, 1992 [JP] Japan ..................................... 4-158500

[51] Int. Cl.$^6$ .............................. B29C 65/30; H05B 3/10; H05B 3/16; H05B 3/20
[52] U.S. Cl. ........................................................ 219/543
[58] Field of Search ..................... 219/543, 544, 219/528; 338/306, 307, 308, 309, 314; 252/514

[56] References Cited

U.S. PATENT DOCUMENTS

| | | | |
|---|---|---|---|
| 2,859,321 | 11/1958 | Garaway | 219/543 |
| 2,939,807 | 6/1960 | Needham | 219/543 |
| 3,830,656 | 8/1974 | Takenaka et al. | 338/308 |
| 3,833,410 | 9/1974 | Aug et al. | 338/308 |
| 3,934,119 | 1/1976 | Trenkler | 219/543 |
| 3,944,787 | 3/1976 | Jost | 219/543 |
| 4,130,671 | 12/1978 | Nagesh et al. | 252/512 |
| 4,342,020 | 7/1982 | Utner et al. | 338/308 |
| 4,415,486 | 11/1983 | Boonstra et al. | 338/308 |
| 4,501,951 | 2/1985 | Benin et al. | 219/243 |
| 4,507,119 | 3/1985 | Spencer | 604/280 |
| 4,545,928 | 10/1985 | Kano et al. | 252/518 |
| 4,633,063 | 12/1986 | Willis | 219/243 |
| 4,647,756 | 3/1987 | Willis | 219/243 |
| 4,827,108 | 5/1989 | Balderson | 219/543 |
| 4,864,101 | 9/1989 | Shaposka et al. | 219/243 |
| 5,026,970 | 6/1991 | Buttery | 219/543 |
| 5,096,619 | 3/1992 | Slack | 252/514 |
| 5,155,800 | 10/1992 | Rezabek et al. | 219/543 |
| 5,221,644 | 6/1993 | Berlin et al. | 252/514 |
| 5,252,944 | 10/1993 | Caddock, Jr. | 338/309 |

FOREIGN PATENT DOCUMENTS

| | | |
|---|---|---|
| 0103977 | 3/1984 | European Pat. Off. . |
| 0158779 | 10/1985 | European Pat. Off. . |
| 2329424 | 1/1975 | Germany . |
| 59-49925 | 3/1984 | Japan . |
| 61-30582 | 7/1986 | Japan . |

OTHER PUBLICATIONS

Emily Heine, Du Pont Magazine, "Hot Idea: Print a Heater," vol. 57, No. 1, Feb. 1, 1963, pp. 19–21.

*Primary Examiner*—Geoffrey S. Evans
*Attorney, Agent, or Firm*—Burns, Doane, Swecker & Mathis

[57] ABSTRACT

A heater element consisting of a metal plate, an insulating layer formed on one side of the plate, and a resistor of screen printed conductive paste including silver particles is in a winding pattern on the insulating layer. A pair of terminals are connected to the ends of the resistor. The plate has two halves along a fold-line with two holes formed so that when the heater element is folded along the fold-line the holes are disposed respectively over the terminals.

18 Claims, 5 Drawing Sheets

HEATER ELEMENT FOR A TUBE CONNECTING DEVICE

BACKGROUND OF THE INVENTION

1. Field of the Invention

This invention relates to a heater element suitable for use in a tube connecting device, wherein a set of tubes are melted and cut to be connected with each other by heating under a sterilized condition.

2. Description of the Related Art

When a dialysate bag and/or a waste liquid bag are changed in a continuous ambulatory peritoneal dialysis (CAPD), for example, or when tubes are connected to a blood-collecting bag and/or a blood component bag in a blood transfusion system, it is necessary to connect the tubes with each other in a sterilized condition.

There has been disclosed a tube connecting device for use in the situation like above, which connects a set of tubes with each other by heating and melting ends of the tubes in a sterilized condition (see U.S. Pat. No. 4,507,119).

The disclosed tube connecting device comprises a set of blocks capable of holding in parallel two tubes to be connected with each other, and a wafer (plate-shaped heater element) movably disposed between the blocks so that it can transversely cross the tubes. The wafer is heated while the two tubes are held by the blocks in parallel and in opposing directions with each other. The heated wafer is moved to melt and cut the tubes. Then, one of the blocks is moved relative to the other block in a direction perpendicular to the tube until the axes of the two tubes meet together in a line, and the wafer is removed. The melted ends of the tubes are fused together.

The wafer employed in the tube connecting device of this type is provided with a resistor disposed between folded metal plates having insulation layers (adhesive layers). When the resistor is fed with electricity, it generates heat so that the entirety of the metal plate is heated (see U.S. Pat. No. 4,501,951).

The resistor of the wafer is formed by etching a stainless foil or a nickel-chromium foil, which is accompanied by the following disadvantage.

(1) The stainless foil or the like used there is manufactured by a thin plate rolling process and has the thickness of about 25 μm, which usually shows an appreciable variation. The width of the resistor also varies due to the limitations of the etching process. Thus, the resistance of the resistor cannot be stably obtained, namely, an error within ±5% in the designed resistance (eg 10.5Ω) can hardly be achieved.

(2) It is difficult to adjust the resistance of the resistor, since the resistor is formed of stainless foil or the like having the predetermined thickness and excessive etching can occur.

(3) The resistor made of stainless foil or the like is hard to adhere to the insulation layer of the wafer, since air is apt to enter into the gap between the resistor and the insulation layer. Hence, a portion of the resistor is often peeled off during manufacture of the wafer and the resistance of the resistor is caused to vary. When the resistor is in use, an expansion in the wafer thickness occur sometimes due to a temperature difference across the wafer and an increase in plate thickness. As a result, an imperfect fusion of the tubes is effected and leakage of the collected blood may occur by the imperfectly-connected tubes.

(4) Manufacturing the resistor by etching process requires a number of manufacturing steps, a long manufacturing time and high manufacturing costs.

Once the wafer has been used, it may preferably be discarded because the surface of the wafer is contaminated with melted resin of the tubes or blood contained in the tubes. For this purpose, an invention has been devised thereby it becomes possible to judge if the wafer is not new (see U.S. Pat. No. 4,647,756).

This wafer, having the above-described function, comprises a bypass fuse which is electrically connected between both terminals of the resistor. When the wafer is new, the voltage applied across the both terminals of the resistor causes the current to bypasses the resistor and flow in the fuse. After the fuse has been burnt out, the current flows in the resistor to generate heat. When the wafer is not new, the fuse is already gone. Therefore, when the voltage is applied across both terminals, the current flows in the resistor directly. It can be determined, based on the difference between rise patterns of the applied voltages, whether the wafer is new or old. In this arrangement, an additional manufacturing step to connect the fuse is required after the resistor has been formed by etching, which however, brings an increase in the number of manufacturing steps, the manufacturing time and the manufacturing costs.

SUMMARY OF THE INVENTION

It is the object of the present invention to provide a heater element suitable for use in a tube connecting device, wherein resistance of a resistor can be stably obtained with an ease of adjustment.

According to the present invention, for achieving the above object, there is provided a heater element suitable for use in a tube connecting device, which comprises: a metal plate; an insulation layer formed on one surface of said metal plate; a resistor formed on said insulation layer, for electrically generating heat; and terminals respectively connected to both ends of said resistor, wherein at least said resistor is produced by a screen printing process, whereby a desired pattern of a conductive paste is printed and hardened.

The resistor in the heater element can be formed by evaporizing solvent from a binder so as to solidify the binder after the desired pattern of the conductive paste has been printed by the screen printing process, so that the resistance of the so formed resistor is further varied by denaturation of the binder under electrical heating of said resistor itself.

According to the heater element of the present invention for the tube connecting device, as has been described above, since the resistor is formed by the screen printing method, the accuracy of dimensions of the resistor is improved. When the resistor is mass-produced, a variation in its resistance value is extremely low. Further, the resistance value of the resistor can be easily adjusted by varying the screen printing conditions.

Compared with the case where the resistor and the like are manufactured by etching, the number of steps for manufacturing the resistor and the like can be reduced and the resistor and the like can be easily manufactured. Further, the manufacturing time can be shortened and the manufacturing cost can be greatly reduced. Accordingly, the resistor and the like are suitable for the mass-production.

Further, since the resistor and the like produced by the screen printing method are not deteriorated and the properties of adhesion between the resistor and the like and the insulative layer are excellent, the resistor and the like are prevented from being separated out of the insulative layer.

According to the heater element of the present invention, which has the resistor whose resistance value varies before and after its energization and is suitable for use in the tube connecting device, it can be determined, based on the result of measurement of the resistance value of the resistor, for example, which has been effected before its use, whether or not the heater element is new or old.

The above and other objects, features and advantages of the present invention will become apparent from the following description and the appended claims, taken in conjunction with the accompanying drawings in which a preferred embodiment of the present invention is shown by way of illustrative example.

DETAILED DESCRIPTION OF THE PREFERRED EMBODIMENTS

Figure 1:
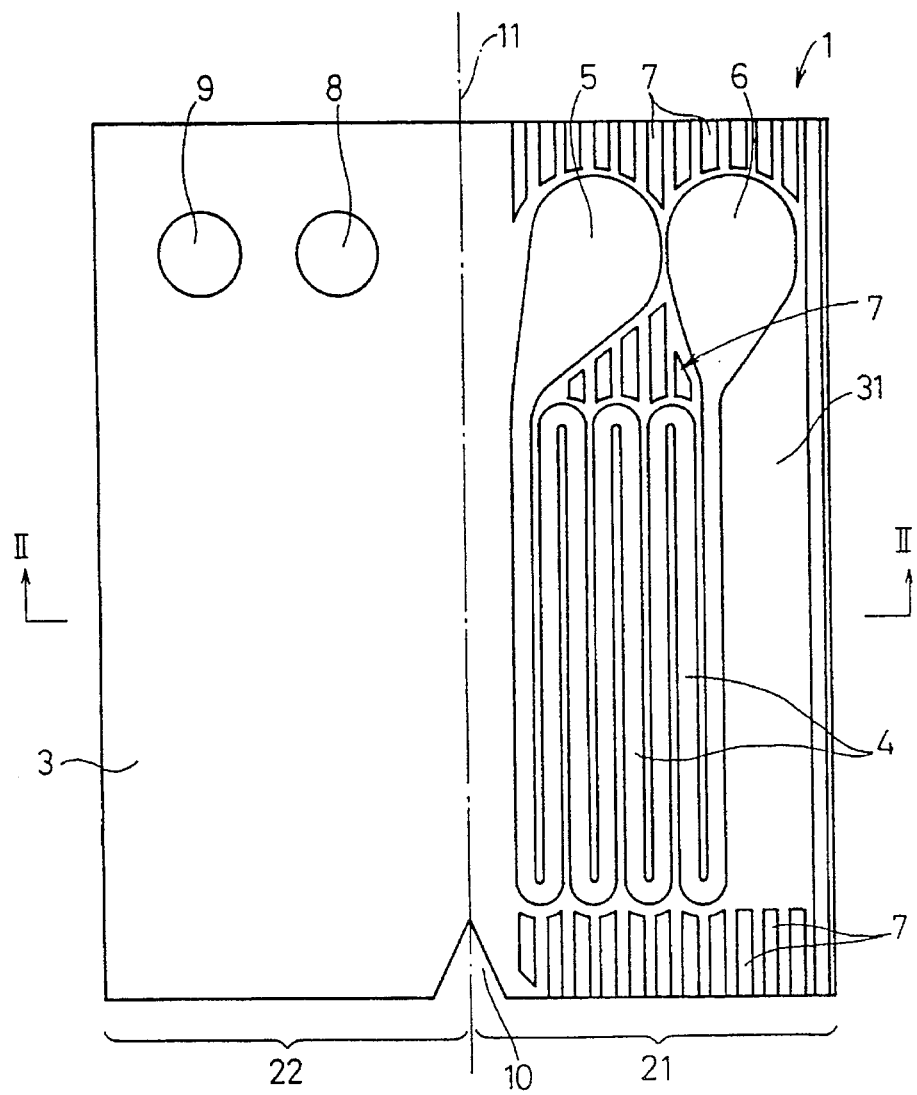
FIG. 1 is a plan view showing one example of the structure of a heater element in a unfolded form according to the present invention.
Figure 2:
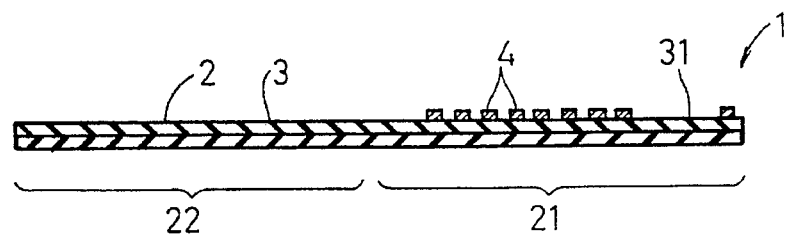
FIG. 2 is a cross-sectional view taken along line II—II of FIG. 1.

FIG. 1 is a plan view showing one example of the structure of a heater element (hereinafter called "wafer") in a unfolded form according to the present invention, which is suitable for use in a tube connecting device. FIG. 2 is a cross-sectional view taken along line II—II of FIG. 1. As shown in FIGS. 1 and 2, a wafer 1 comprises a metal plate 2, an insulation layer 3 formed substantially over the entire internal surface (i.e., the inner surface formed when the metal plate 2 is folded about a bend line 11 to be described later) of the metal plate 2, a resistor 4 which is formed on one surface of the insulation layer 3 which generates heat by electricity, and terminals 5 and 6 having relatively large areas which are respectively electrically connected to both ends of the resistor 4.

The metal plate 2 is made of a metal having an superior thermal conductivity to allow heat to be uniformly distributed along the surface of the metal. An exemplary suitable metal includes, for example, copper, aluminum, gold, silver, iron or alloy including these metals. Of these, copper or copper alloy with a copper content of 99.9% or higher by weight is particularly preferred. This type of metal is preferred because of uniformity of heating and the ease of processing.

Suitable thickness of the metal plate 2 depends on the material. However, the metal plate 2 may preferably have a thickness range of from 0.08 mm to 0.12 mm, particularly, 0.95 mm to 0.105 mm. If the thickness of the metal plate 2 is thicker than these values, then a difficulty in fusing of cut portions of the tubes arises. If, on the other hand, the thickness of the metal plate 2 is thinner than these values, then a difficulty in melting and cutting of the tubes arises.

The insulation layer 3 formed on the internal surface of the metal plate 2 electrically insulates the resistor 4 from the metal plate 2. Further, the insulation layer 3 serves as an adhesive layer to adhere a half plate 21 of the metal plate 2 on which the resistor is formed (a resistor constitutive portion 21) and another half plate 22 on which no resistor is formed (a resistor non-constitutive portion 22). The two halves 21 and 22 are folded and stuck to each other. Therefore, the insulation layer 3 is required to maintain a desired adhesive force (secondary adhesive force) even after it has been printed, heated and dried.

Thus, materials for the insulation layer 3 may preferably have along with electrical insulating properties, heat-resisting properties (300° C. to 350° C.), solvent-resisting properties and flow-resisting properties, and may include, for example, epoxy resin, acrylic adhesive, room-temperature hardening type silicone adhesive, polyimide adhesive, polyimide resin, a modified acrylic adhesive, silicone-modified polyimide adhesive, etc.

The thickness of the insulation layer 3 is set to such a thickness that sufficient insulating properties between the resistor 4 and the metal plate 2 is secured. It may preferably range from 15 μm to 50 μm, particularly from 20 μm to 35 μm, depending on the materials. If the insulation layer 3 is excessively thick, then it bocomes hard to transfer the heat through the insulation layer 3. If the insulation layer 3 is excessively thin, on the other hand, it becomes hard to obtain a desired thickness of the heater element 1 formed by folding the metal plate 2.

The insulation layer 3 may be formed, for instance, by applying a liquid including one of the. above adhesive materials or their precursors on the internal surface of the metal plate 2 and hardening it.

On the insulation layer 3 formed on the resistor constitutive portion 21 side, there are formed the resistor 4 shaped in a desired pattern, the terminals (electrodes) 5 and 6 respectively electrically connected to both ends of the resistor 4, and a plurality of bars 7 arranged in noncontact with the resistor 4 and the terminals 5 and 6, the bars 7 being disposed around the terminals 5 and 6 and on one end of the resistor constitutive portion 21, which is located on the side opposite to the terminals 5 and 6. The resistor 4, the terminals 5 and 6 and the bars 7 (hereinafter called generically "resistor 4, etc.") are formed by a screen printing process or formed in a lump if appropriate.

In the present invention, the resistor 4, etc. may be formed by performing the screen printing process plural times. For example, after forming a combination of the resistor 4 and bars 7 with conductive paste of a composition, the terminals 5 and 6 may be formed with conductive paste of a different composition.

Grooves S are respectively defined between the adjacent bars 7. The grooves S are provided to discharge gas produced in the insulation layer 3 when the resistor constitutive portion 21 and the resistor non-constitutive portion 22 are bonded together under heat and pressure, along with gas produced in the semi-hardened resistor 4, to the outside. Further, the bars 7 can serve to maintain the thickness of the wafer 1 uniform.

Now, a description on the forming of the resistor 4, etc. will be given below in further detail.

First, the conductive paste is printed on the insulation layer 3 of the resistor constitutive portion 21 in a desired pattern by using the screen printing process.

Conductive substances, which are major components of the conductive paste, are normally metallic particles. Among these, silver or silver alloy is particularly preferred.

As silver alloy, there may be Ag—Pd alloy, Ag—Pt alloy, Ag—Pd—Pt alloy or the like. Silver alloys containing Pd have excellent migration-resisting properties as compared with pure silver.

In a conductive paste, either silver or silver alloy normally exists in the form of particles, in order to increase intervals between the respective particles. The average diameter of the particles may preferably range from 0.5 µm to 50 µm, particularly, from 1 µm to 10 µm. If the average diameter of the particles is less than 0.5 µm, then the degree of shrinkage of the resistor 4, etc. becomes large. If, on the other hand, the average diameter of the particles is larger than 50 µm, then the printing properties and the dispersion properties of the conductive paste are lowered.

Vehicles of a conductive paste may include: binder such as epoxy resin, thermoset melamine resin, acrylic resin, nitrocellulose, ethylcellulose, phenolic resin, vinyl resin or the like; solvent such as butylcarbitol, terpineol or the like; thermoplastic resin such as polyvinyl chloride for improving thermoplasticity; dispersant; activator; viscosity modifier; film adhesive-force accelerating substance (eg, metallic oxide); resistance regulating substance; etc. Among these, desired ones can be suitably mixed according to the purpose.

It may be preferable for a conductive paste to contain the vehicles in an amount of from about 10 to 75 wt. %. The conductive paste may preferably have a viscosity ranging from 300 Ps to 400 Ps (at 25° C.) from the view point of printing properties and reproducibility of the resistor.

When the aforementioned conductive paste is used for the screen printing process, it is preferable to employ a screen having a mesh of 180 to 300, particularly, a mesh of 200 to 250.

The film thickness of the resistor 4, etc. in a hardened state may preferably range from about 10 µm to 40 µm, more preferably, about 20 µm to 30 µm. This is because a desired heat can be generated. The film thickness can be easily set by varying conditions in the screen printing process, such as the thickness of screening emulsion, the rubber hardness of squeegee, an interval between the screen and an object to be printed, the rate of movement of the squeegee, etc.

In the present invention, the conditions such as the composition, viscosity and film thickness of the conductive paste may differ in each of the resistor 4, the terminals 5 and 6 and the bars 7.

Next, the conductive paste printed in the predetermined pattern on the insulation layer 3 is dried and hardened using an oven or a hot-air type drier. Suitable conditions for drying and hardening the conductive paste may be about 150° C. to 200° C. in temperature and about 5 to 30 minutes in time.

It is preferable to set the resistance of the so-formed resistor 4 to range from 8Ω to 16Ω, particularly from 8Ω to 12Ω.

Accuracy in dimensions of the resistor is improved, since the resistor is formed by the screen printing process, and an extremely low variation in resistance of the resistor can be attained. That is, an error within ±5%, particularly within ±1.5%, in the resistance can be achieved. Further, the resistance of the resistor can easily be adjusted by varying conditions in the screen printing process.

The number of manufacturing steps, manufacturing time and manufacturing costs can greatly be reduced, even when a complex and fine pattern of the resistor 4, etc. is employed, compared to the conventional etching process of manufacturing the resistor.

Further, the resistor 4, etc. produced by the screen printing process adhere to the insulation layer 3 firmly enough to prevent the resistor 4, etc. from being peeled off from the insulation layer 3 during production.

Moreover, the resistor 4, etc. produced by the screen printing process have excellent heat-resistant properties. Deterioration, such as a crack in the film, is hard to occur even under a rapid temperature change, particularly, under a temperature rise at the time when the resistor constitutive portion 21 and the resistor non-constitutive portion 22 are bonded together under heat and pressure, as described later.

In forming the resistor 4, etc., a main adhesive portion 31 in which the resistor 4, etc. are not formed may preferably be provided on the side (right side as viewed in FIG. 1) opposite to the bend line 11 of the resistor constitutive portion 21. A strong adhesive force between the resistor constitutive portion 21 and the resistor non-constitutive portion 22 when they are stucked together can be provided by the main adhesive portion 31.

Figure 3:
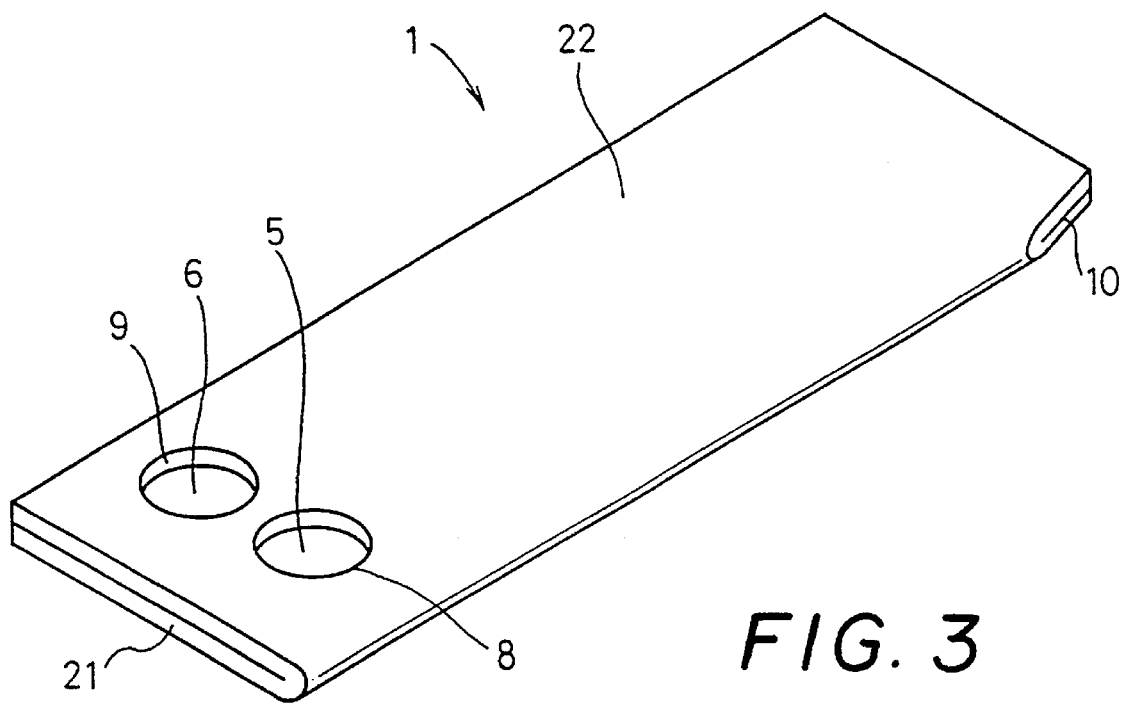
FIG. 3 is a perspective view showing the example of the structure of the heater element shown in FIG. 1 in a folded form.

As shown in FIG. 1, the resistor non-constitutive portion 22 has two openings 8 and 9 defined therethrough. When the metal plate 2 is bent along the bend line 11 and the resistor constitutive portion 21 and the resistor non-constitutive portion 22 are stucked together, the openings 8 and 9 are located in positions respectively corresponding to the terminals 5 and 6. As shown in FIG. 3, central portions of the terminals 5 and 6 are exposed through the openings 8 and 9 when the metal plate 2 is folded, to which an electrical source is connected.

Incidentally, the shape of the openings 8 and 9 is not necessarily limited to the circle shown in FIG. 1. It can be an ellipse, a triangle, a square, a hexagon or the like.

After the resistor 4, etc. have been formed, the metal plate 2 is folded along the bend line 11 so that the resistor 4, etc. are included inside. Simultaneously, the resistor constitutive portion 21 and the resistor non-constitutive portion 22 are stucked together and bonded to each other under heat and pressure to complete the heating element or wafer 1 shown in FIG. 3.

The heat and pressure conditions in the bonding of the resistor constitutive portion 21 and the resistor non-constitutive portion 22 are decided depending on the materials and thickness of the insulation layer 3. However, a temperature ranging from 170° C. to 260° C. and a pressure ranging from 5 kg/cm$^2$ to 40 kg/cm$^2$ are preferable.

A cut portion 10 shaped in the form of a triangle, for example, may be provided in the corner of the wafer 1, on the side opposite to where the openings 8 and 9 are and positioned on the bend line 11, as shown in FIG. 3. The cut portion 10 serves as a guide in moving the wafer 1.

The wafer 1 may be manufactured one by one, however, it is more preferable to produce plural wafers at once, from the productivity point of view. In this situation, a plurality of insulation layers 3 and resistors 4 are formed simultaneously on a large metal plate, individual metal plate 2 is cut from the large one, and the openings 8 and 9 are formed in each of them by a punching process, for example.

Now, a description will be made on the structure of a tube connecting device using the wafer 1 according to the present invention.

Figure 4:
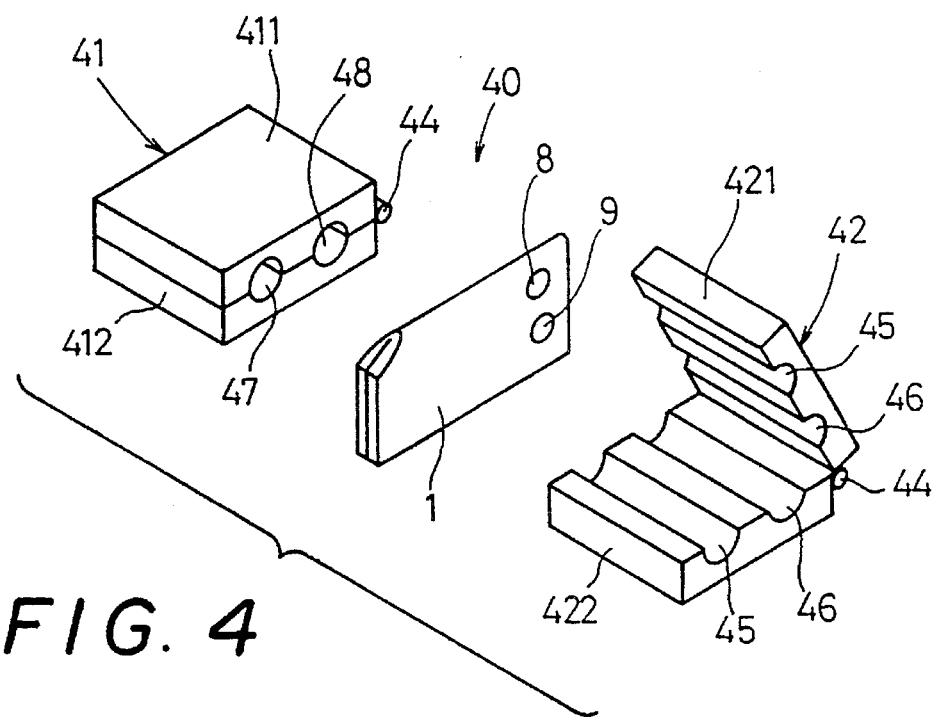
FIG. 4 is a perspective view illustrating one example of the structure of the tube connecting device.

FIG. 4 is a perspective view showing one example of the structure of a tube connecting device 40. FIGS. 5 through 8 are respectively perspective views illustrating steps for connecting tubes 14 and 15 to one another using the tube connecting devices 40. Apparent from the figures, the tube connecting devices 40 comprises a set of holders 41 and 42, and a wafer 1 according to the present invention replaceably disposed between the holders. Two tubes 14 and 15, made of polyvinyl chloride, for example, are held side by side in the holders 41 and 42, respectively, and melted and cut by the heated wafer 1. While cut ends of the tubes 14 and 15 are in a melted state, one of the holders, 41, is moved, and then the wafer 1 is removed. Thereafter, the melted ends of the tubes 14 and 15 are fused together.

The holders 41 and 42 respectively comprise holder components 411, 412 and 421, 422 as the upper and lower sides of the respective holders. The holder components 411 andg 421 are respectively swingable about supports 44.

Grooves 45 and 46 each having a semicircular cross-section are respectively provided in the opposing inner surfaces of the holder components 411 and 412. The holder components 421 and 422 also have the same grooves. Thus, a pair of holes 47 and 48 for holding tubes therein are formed in the holder 41 when the holder components 411 and 412 are closed. The holes 47 and 48 are formed also in the holder 42. A tube clamper (not shown) for pressing and blocking the tube when the holder components 411 and 412 (421 and 422) are closed may be provided inside of each of the holes 47 and 48 of the respective holders.

How to use the tube connecting device 40 will now be described below.

Figure 5:
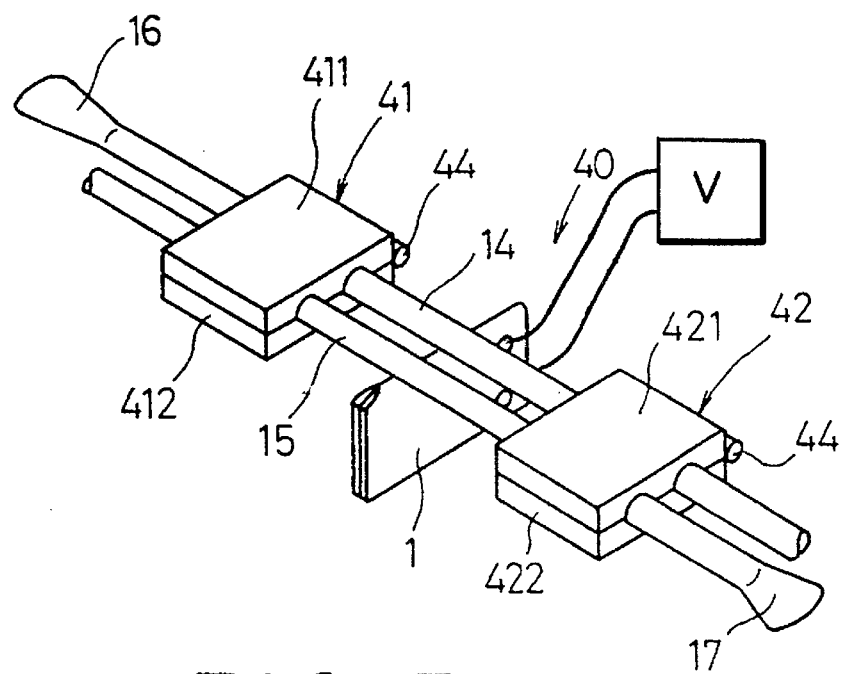
FIG. 5 is a perspective view showing a step for connecting tubes using the tube connecting device shown in FIG. 4.

As shown in FIG. 5, the tubes 14 and 15 are laid in parallel for a predetermined length in such a manner that closed ends 16 and 17 of the tubes 14 and 15 directing opposite to each other. Then, the tubes 14 and 15 are respectively inserted into the Grooves 45 and 46 of the holders 41 and 42. Thereafter, the holder components 411, 412 and 421, 422 are closed so that the two tubes 14 and 15 are fixedly held by the holes 47 and 48.

Next, a voltage of 15 V to 24 V, for example, is applied across the terminals 5 and 6 of the wafer 1 by an voltage applying means V to cause an electric current to flow in the resistor 4 of the wafer 1. The resistor 4 generates heat and hence the wafer 1 is heated to a temperature (of about 260° C. to 320° C., for example) higher than the melting point of the tubes 14 and 15.

Figure 6:
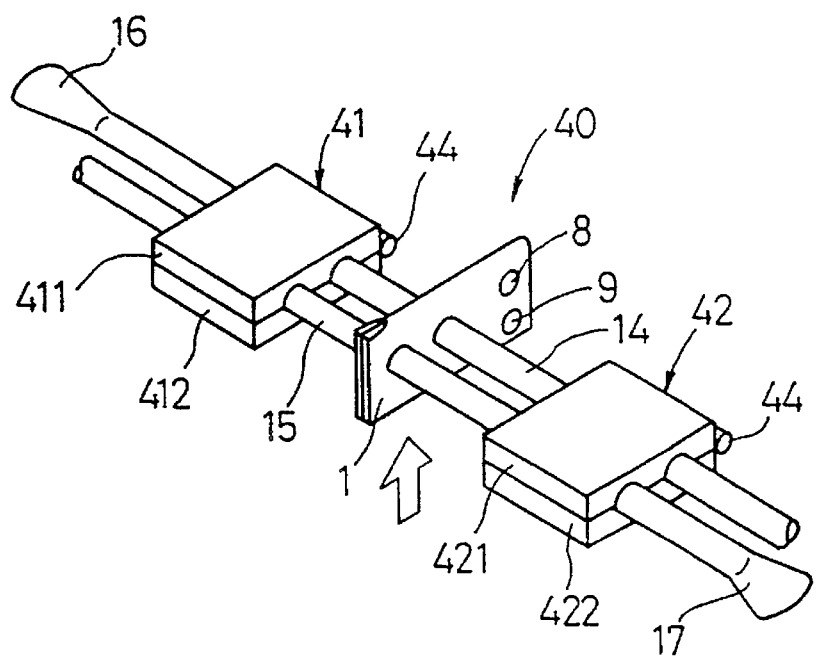
FIG. 6 is a perspective view illustrating another step for connecting tubes using the tube connecting device shown in FIG. 4.

When the wafer 1 is moved upward as shown in FIG. 6 in this condition, the tubes 14 and 15 are melted and cut by the heat of the wafer 1. At this time, the cut ends of the tubes 14 and 15 are at a high temperatures under a melted or softened state, and not in communication with the outside since the wafer 1 is in contact with the cut ends, a sterilized state is maintained there.

Figure 7:
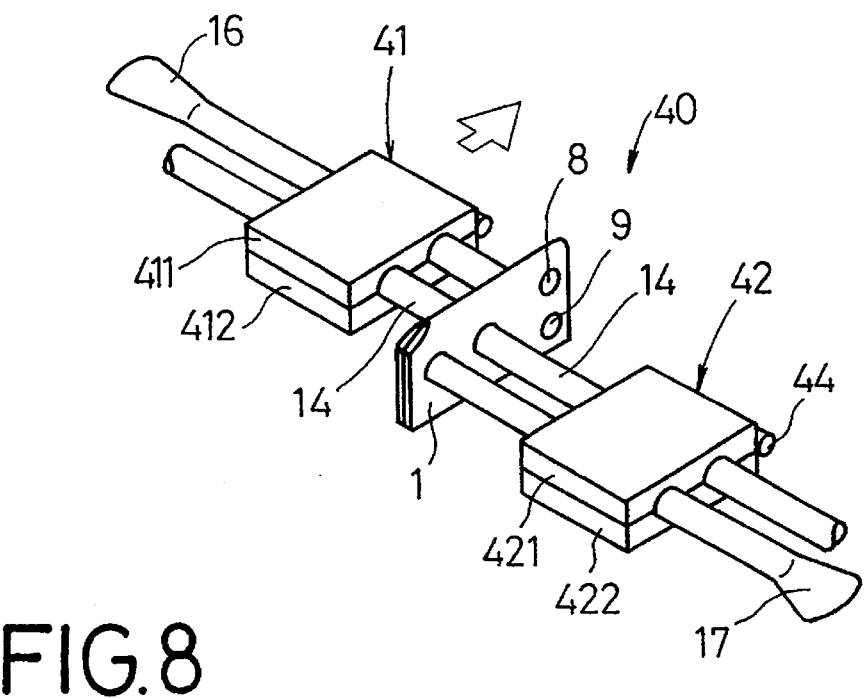
FIG. 7 is a perspective view depicting a further step for connecting tubes to each other using the tube connecting device shown in FIG. 4.

While the cut ends of the tubes 14 and 15 are being held in the melted state, the holder 41 is moved in a direction indicated by the arrow in FIG. 7. Thereafter, the holder 41 is stopped and fixed at the position where the sections of the cut tubes 14 and 15 are facing to each other.

Figure 8:
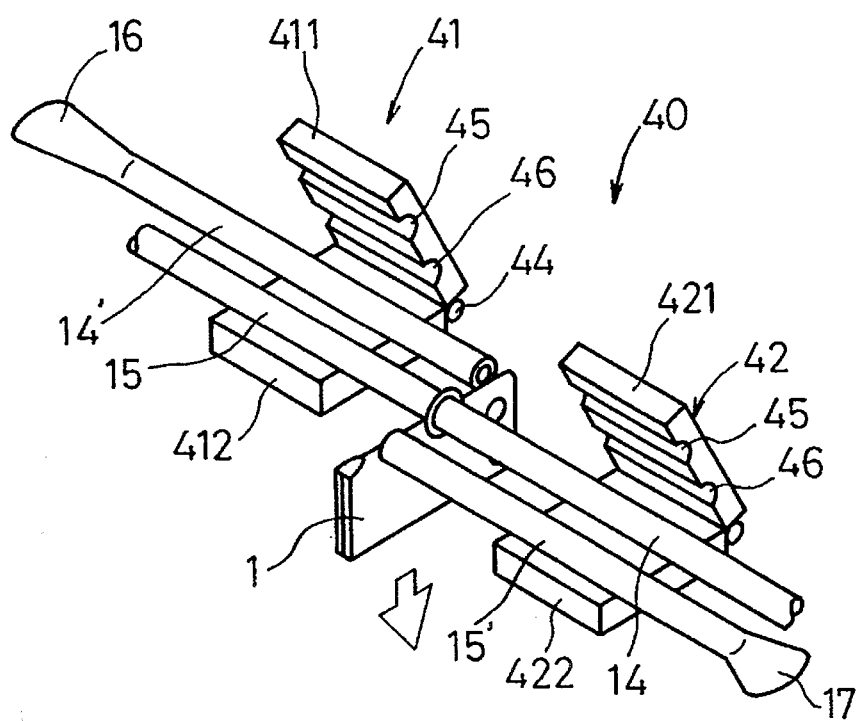
FIG. 8 is a perspective view showing a still further step for connecting tubes using the tube connecting device shown in FIG. 4.

Next, the wafer 1 is pulled out downward as shown in FIG. 8. Thereafter, the holder 41 is pressed toward the holder 42 as necessary. As a result, the sections of the melted tubes 14 and 15 are fused together so that both tubes 14 and 15 are coupled to each other.

In a series of operations from the cutting to the connection of the tubes 14 and 15 using the wafer 1, the sections of the tubes 14 and 15 and their peripheral areas are at the high temperature in the melted or softened state. Further, the sections of the tubes contact closely to the surface of the wafer 1 which is maintained at a high temperature, and are hindered from communicating with the outside, until the connection is completed. Thus, the sterilized state of the tubes is perfectly maintained.

After the tubes 14 and 15 have been connected, tube members 14' and 15' including the closed ends 16 and 17 are removed to be discarded.

It is desirable that the used wafer is replaced with a new wafer 1 when other tubes are cut and connected. That is, a disposable or single use of the wafer 1 is preferred in the invention. This necessitates the wafer to provide detectability of whether the wafer is new or not, when it is used.

The wafer according to the present invention is constructed in such a manner that the resistance of the resistor 4 varies before and after its use. Such a wafer may have the same construction as the aforementioned wafer 1 except for the differences which will be described below.

Namely, the conditions (temperature and/or time) of drying and hardening the conductive paste printed to form the resistor 4, etc. on the insulation layer 3 of the wafer 1 are adjusted so that the solvent in the binder of the conductive paste is evaporated to merely solidify the binder. Incidentally, the drying and hardening conditions mentioned above should be determined by considering the heat applied when the resistor constitutive component 21 and the resistor non-constitutive component 22 are bonded to each other under heat and pressure after formation of the resistor 4, etc.

Once such a resistor 4 is energized, it heats itself and the so-solidified binder is further denatured by the heat so that the resistance of the resistor 4 is reduced.

Figure 9:
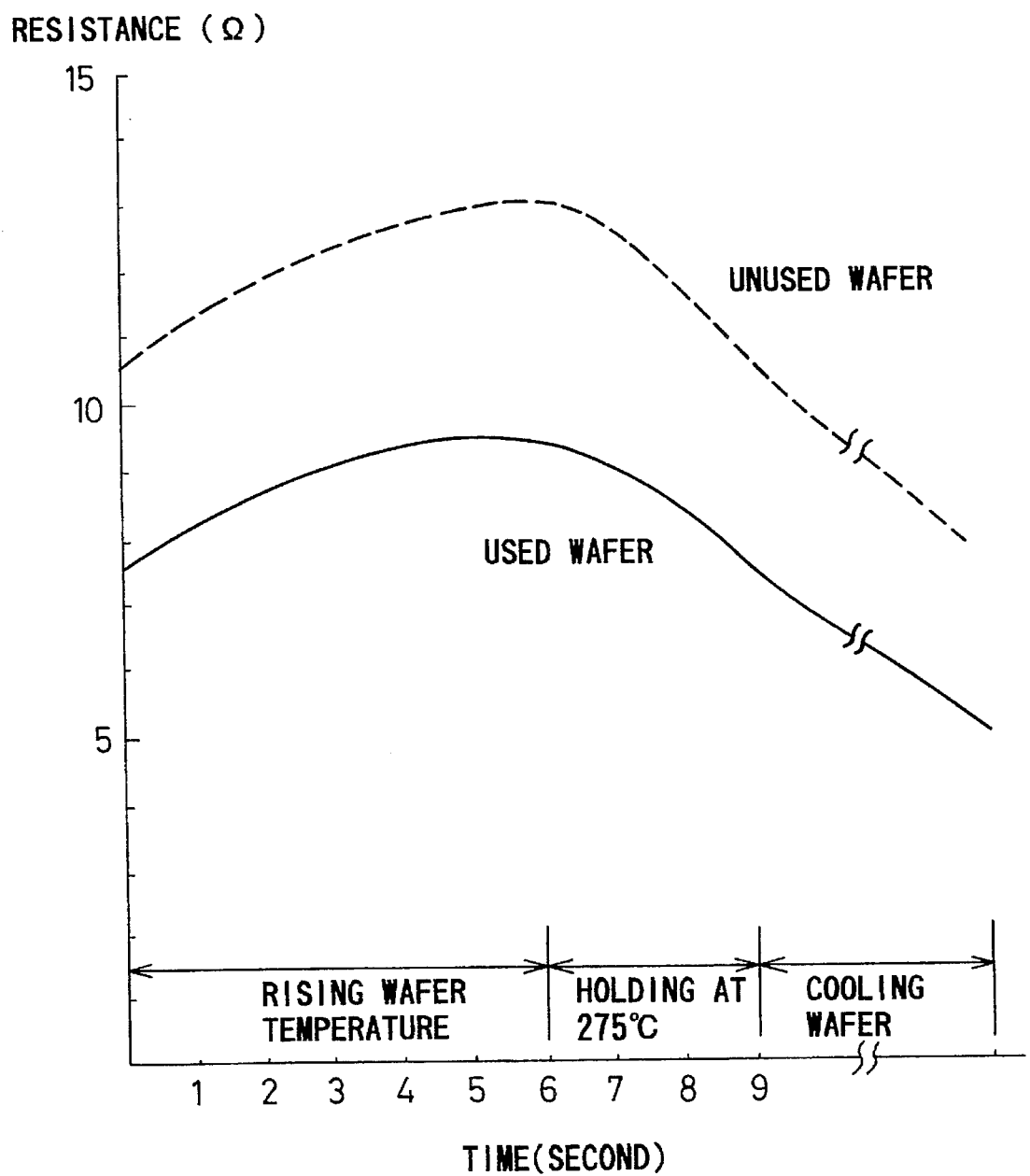
FIG. 9 is a graph illustrating the manner in which the resistance of used and unused resistors change with time.

FIG. 9 is a graph illustrating the manner of variation in the resistance of the resistor 4 with time. The graph shows a change in the resistance of the resistor 4 when a dc voltage (of 15 V to 20 V, for example) is applied across the terminals 5 and 6 of the wafer 1. The surface temperature of the wafer 1 is caused to reach 275° C. after about 6 seconds, the voltage is then controlled so as to maintain the surface temperature of the wafer 1 at 275° C. for 3 seconds, and thereafter the application of the voltage is stopped to cool the wafer 1 down to the room temperature.

As indicated by the graph, a curve indicative of a variation in the resistance of a resistor 4 in an unused wafer (indicated by the dotted line in the graph) differs from that in a used wafer (indicated by the solid line). That is, the resistance of the resistor 4 in the unused wafer is relatively high throughout the entire process, whereas the resistance in the used wafer is low throughout the entire process, because the binder in the conductive paste is denatured by the heat generated during the use of the wafer.

Whether the wafer is new or old can be determined by measuring the resistance (or voltage) of the resistor 4 in a predetermined occasion. Thus, the used wafer can be safely avoided from being re-used inadvertently.

To manufacture such a resistance varying wafer 1, it is only necessary to adjust the conditions of drying and hardening the conductive paste. Such a wafer 1 does not need a change in its circuit configuration and the provision of other parts. Therefore, the easiness and costs in the manufacture of the wafer can be maintained unchanged.

Incidentally, the resistance varying wafer is not necessarily limited to one having the above structure. The wafer may have, for example, a structure in which the resistance of the resistor 4 is varied by denaturation of components of the conductive paste such as the conductive substance, the vehicle or the like, or variation in the orientation or linkage states of the components caused by the application of electricity or a temperature change.

A description has been given above of one example of the heater element according to the present invention. However, the present invention is not necessarily limited to the structure referred to above. For example, the terminals 5 and 6 may be those manufactured by a method other than the screen printing process. Further, the terminals 5 and 6 may be such that are projecting from the outer peripheral edge of the metal plate 2.

In the heater element according to the present invention, since the resistor is formed by the screen printing process, as has been described above, the following advantageous effects are realized.

Accuracy in dimensions of the resistor is improved, and an extremely low variation in resistance of the resistor can be attained. Further, the resistance of the resistor can easily be adjusted by varying conditions in the screen printing process.

The number of manufacturing steps, manufacturing time and manufacturing costs can greatly be reduced, compared to the conventional etching process of manufacturing the resistor.

Further, the resistor produced by the screen printing process adheres to the insulation layer strongly enough to prevent the resistor from being peeled off.

By measuring the resistance of the resistor, it can easily be determined whether the heater element is new or old, since the resistance of the resistor varies before and after the use due to thermal denaturation of binder in the resistor formed of the conductive paste.

Further, the resistor whose resistance value varies before and after its energization can be manufactured by the screen printing method, for example. The resistor can be easily produced by simply controlling the conditions for drying and hardening the conductive paste. It is therefore unnecessary to change a circuit configuration and additionally provide other parts as in the conventional wafer. Further, the heater element according to the present invention can be easily manufactured and the manufacturing cost can also be greatly reduced.

What is claimed is:

1. A heater element, to which a predetermined voltage is applied, suitable for use in a tube connecting device, comprising:

a metal plate;

an insulating layer formed on one surface of said metal plate;

a resistor formed on said insulating layer, for electrically generating heat, said resistor comprising a screen printed conductive paste applied in a winding pattern on said insulating layer, said resistor having first and second end portions;

a pair of terminals connected to said first and second end portions, respectively, of said resistor; and means for applying a voltage across said pair of terminals to cause an electrical current to flow through said winding pattern of screen printed conductive paste for causing said resistor to generate heat;

wherein said winding pattern of screen printed conductive paste is hardened on said insulating layer, and wherein said metal plate is separated into two halves along a fold-line, said resistor and said pair of terminals being formed on one side of said fold line, and two holes being formed in said metal plate on another side of said fold line, said holes being aligned with said terminals such that when said heater element is folded in half along said fold line, said holes are disposed respectively over said pair of terminals.

2. A heater element according to claim 1, wherein said metal plate is made of either copper or copper alloy, said copper alloy containing at least 99.9 weight % of copper.

3. A heater element according to claim 1 or 2, wherein said metal plate has a thickness ranging from 0.08 mm to 0.12 mm.

4. A heater element according to claim 3, wherein said metal plate has a thickness which ranges from 0.09 mm to 0.105 mm.

5. A heater element according to claim 1, wherein a conductive substance of said screen printed conductive paste is either silver or silver alloy.

6. A heater element according to claim 5, wherein said silver or silver alloy comprises particles whose average diameter ranges from 0.5 μm to 50 μm.

7. A heater element according to claim 6, wherein said silver or silver alloy comprises particles whose average diameter ranges from 1 μm to 10 μm.

8. A heater element according to claim 1, wherein a plurality of bars and grooves are provided adjacent to said resistor on said insulating layer, each of said grooves being respectively defined between two bars, for communicating with an outside of the heater element.

9. A heater element according to claim 8, wherein said resistor and said plurality of bars are formed on the same screen printed conductive paste.

10. A heater element according to claim 8, wherein said of said bars has a film thickness ranging from 10 μm to 40 μm after said screen printed conductive paste has hardened.

11. A heater element according to claim 10, wherein each of said bars has a film thickness ranging from 20 μm to 30 μm, after said screen printed conductive paste has hardened.

12. A heater element according to claim 1, wherein an adhesive portion is provided in a vicinity of said resistor on a resistor constitutive portion of said metal plate for bonding said resistor constitutive portion and a resistor non-constitutive portion of said metal plate.

13. A heater element according to claim 1, wherein said screen printed conductive paste includes evaporating solvent and a binder, said evaporating solvent being provided for solidifying the binder after the winding pattern of the screen printed conductive paste has been printed, resistance of said resistor being further variable by denaturation of the binder under electrical heating of said resistor itself.

14. A heater element according to claim 1, wherein said resistor has a film thickness ranging from 10 μm to 40 μm after said screen printed presented conductive paste has hardened.

15. A heater element according to claim 14, wherein said resistor has a film thickness ranging from 20 μm to 30 μm, after said screen printed conductive paste has hardened.

16. A heater element according to claim 1, wherein said insulating layer is made of one material chosen from a group consisting of epoxy resin, acrylic adhesive, silicon adhesive and polyimide adhesive and polyimide resin.

17. A heater element according to claim 1, wherein said insulating layer has a thickness ranging from 15 μm to 50 μm.

18. A heater element according to claim 17, wherein said insulating layer has a thickness ranging from 20 μm to 35 μm.

* * * * *